United States Patent [19]

Semm

[11] Patent Number: 5,362,310
[45] Date of Patent: Nov. 8, 1994

[54] HEATING APPARATUS FOR INSUFFLATOR

[75] Inventor: Kurt Semm, Kiel, Germany

[73] Assignee: Wisap Gesellschaft fur Wissenschaftlichen Apparatebau MbH, Sauerlach, Germany

[21] Appl. No.: 43,913

[22] Filed: Apr. 7, 1993

[30] Foreign Application Priority Data

Apr. 9, 1992 [DE] Germany .................. 4211986

[51] Int. Cl.⁵ ............................................ A61M 13/00
[52] U.S. Cl. ............................................ 604/26; 604/114
[58] Field of Search .................. 128/747; 604/26, 113, 604/114; 606/27-31; 607/96, 98, 104, 107

[56] References Cited

U.S. PATENT DOCUMENTS

| | | | |
|---|---|---|---|
| 1,110,919 | 9/1914 | Gamble | 604/114 |
| 1,493,450 | 5/1924 | Richardson | 604/114 |
| 1,572,300 | 2/1926 | Max | 604/114 |
| 1,995,302 | 3/1935 | Goldstein | 604/114 |
| 4,038,519 | 7/1977 | Foucras | 604/114 |
| 4,048,992 | 9/1977 | Lindemann et al. | 604/26 |
| 4,464,169 | 8/1984 | Semm | 604/26 |
| 5,006,109 | 4/1991 | Douglas et al. | 604/26 |
| 5,152,745 | 10/1992 | Steiner et al. | 604/26 |

FOREIGN PATENT DOCUMENTS 2733650  2/1979  Germany .................. 604/26

*Primary Examiner*—Max Hindenburg
*Attorney, Agent, or Firm*—Keck, Mahin & Cate

[57] ABSTRACT

The invention relates to a heating apparatus, which, in conjunction with insufflators for introducing gas into a biological body, for avoiding catarrh to the peritoneum, pleura, etc., heats the greatly pressure-reduced gas to a temperature roughly corresponding to the body temperature. Use is made of a heating hose provided with a heating wire coil.

23 Claims, 1 Drawing Sheet

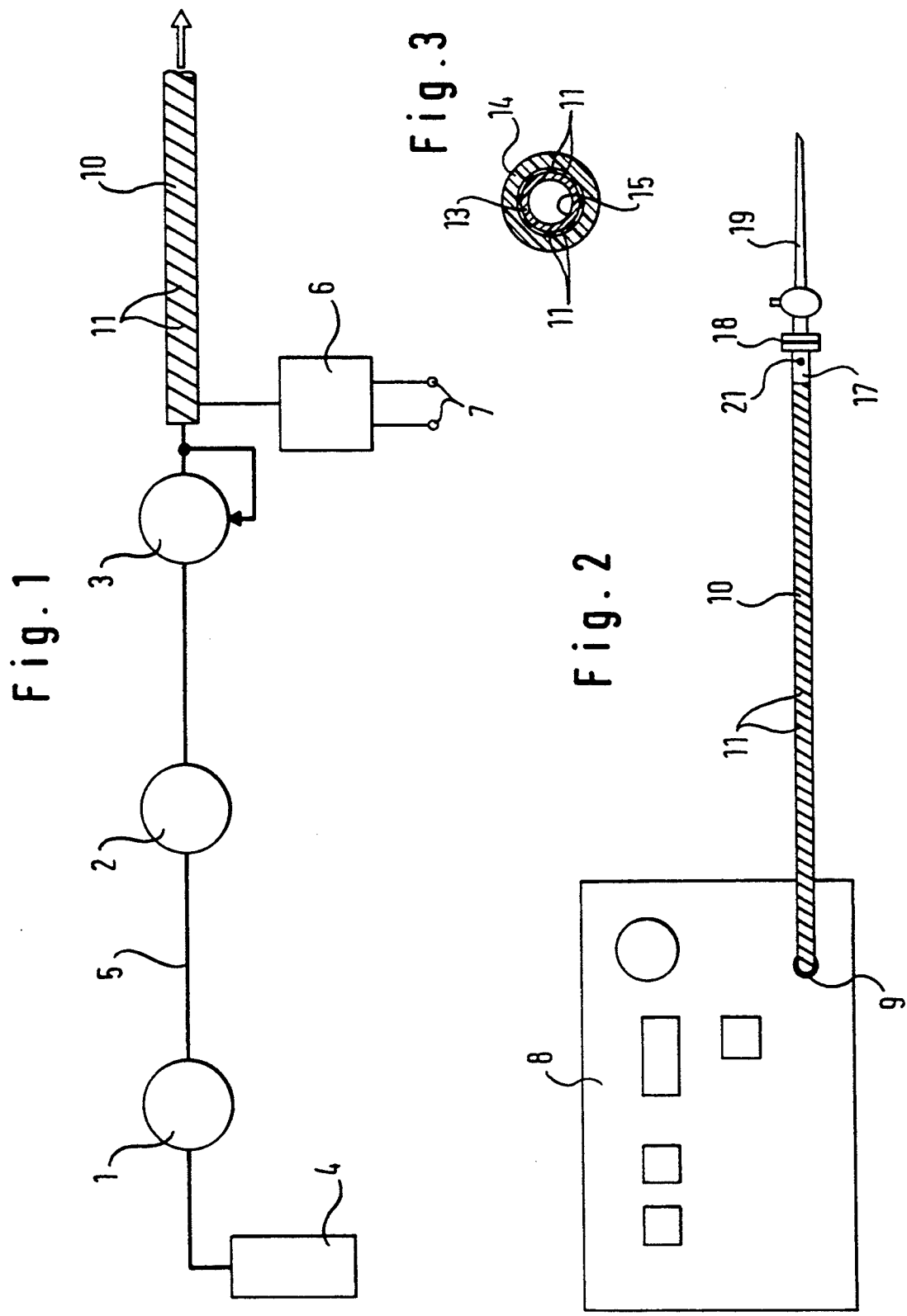

HEATING APPARATUS FOR INSUFFLATOR

BACKGROUND OF THE INVENTION

The invention relates to a method for the insufflation of a $CO_2$ gas in a biological body, in which the pressure of the gas is reduced by means of at least one pressure reducing stage and is subsequently insufflated into the biological body, as well as to a heating apparatus for a pressure-reduced $CO_2$ gas to be introduced into a biological body and which is insufflated into the body by means of an insufflator and a hose line emanating therefrom.

In the case of medical examinations or surgical interventions in the vicinity of the abdomen or thorax pelviscopy, use is made of insufflators with the aid of which a gas, e.g. $CO_2$ or $N_2O$ gas, is insufflated into the corresponding body cavity. This gas supplied at a relatively low overpressure of e.g. 14 to 50 mm/Hg to the corresponding body cavity and which is postoperatively resorbed by the body, makes it possible for the surgeon to endoscopically examine or surgically treat the corresponding organ or tissue area. Therefore such insufflators are adequately known in modern endoscopic surgery.

One problem which has not been solved up to now is that the gas reduced to the necessary, desired pressure by means of different pressure reducing stages at present has a temperature of 16° to 24° C. at the outflow nipple or fitting of the insufflator and is insufflated into the body at this temperature, which medically speaking is well below the body temperature.

This relatively low temperature is due to the fact that the gas is supplied from a liquid pressure cylinder at a pressure of approximately 60 bar and ambient temperature of approximately 23° C. to the insufflation hose. The gas expanded from liquid by pressure reduction over several stages initially leads to an extreme temperature reduction due to the volume expansion of the gas to well below 0° C.

It is admittedly possible within the lines of the insufflator and in particular in the insufflation hose, to raise the temperature to approximately 21° C., so that the $CO_2$ gas insufflated into the body roughly has this temperature, but it is still well below the body temperature of 37° C.

The temperature difference between the insufflated gas and the tissue with a body temperature of 37° C. can lead to catarrhal effects in the abdomen and therefore to pains of a non-specific nature, which have not yet been accurately medically diagnosed.

Consequently there is a medical need to equal out this temperature difference between the insufflated gas and the body temperature in order to avoid any non-specific medical discomfort for the patient.

Attempts to heat the $CO_2$ gas during an insufflation process by means of a hot water bath, by passing the gas through a V2A line at a temperature of approximately 50° C., have a poor efficiency during heating, while the line length, too, is unsatisfactory.

Another alternative of passing the gas through a small heating box containing a heating star, had to be abandoned for various reasons. The problems were in particular that the gas can be excessively heated, which can particularly occur with a very low gas flow and a subsequently necessary high flow.

In addition, the heating box cannot be used as it is not medically sterile, because the moisture and heat formed in the said box would constitute an ideal medium for fungus, so that there would be a considerable contamination risk.

In addition, there are obviously the medically necessary sterilization criteria, the equipment being exposed to a temperature of approximately 134° C. e.g. in the case of steam sterilization. A gas sterilization would also be conceivable, e.g. with ethylene oxide at approximately 60° C., but this would have to take place over a long period of time and this will not be allowed in the future.

SUMMARY OF THE INVENTION

Based on these problems, the object of the invention is to overcome the above problems from the method standpoint and provide an inexpensive heating apparatus for an unreal gas, which fulfils the medical requirements and which can optionally be connected to existing insufflators in the form of a supplementary set.

According to the invention this object is achieved by heating the corresponding gas and by a heating apparatus in which the hose line is constructed as a heating hose.

An essential idea of the invention is based on not, as hitherto, passing the gas to be insufflated into the biological body at roughly ambient temperature, but instead to largely adapt the gas to the body temperature, so that disadvantageous effects on the body can be avoided. This normally means heating the gas from ambient temperature approximately 37° C.

With respect to the largely standardized insufflators, which have a single outlet as a line connecting nipple or fitting for the line leading to the patient and also simultaneously as a measuring outlet and inlet, the invention positions a heating hose between said insufflator outlet and the distal side Veress needle located at the end of the line. Preferably this heating hose comprises several hose casings or jackets, which are e.g. extruded from sterilizable material. A silicone or PU material is particularly suitable for this purpose. In the vicinity of the inner wall of the heating hose, which can optionally also be between the two hose casings, is provided a heating wire, particularly in the form of a heating wire coil, which can also be directly coextruded.

Alternatively it is also possible to have a longitudinal orientation of the heating wires, which can be electrically interconnected, e.g. by welding at the distal side, apart from a conductor as the return conductor. Although silicone is not a good heat conductor, it has surprisingly been found in connection with $CO_2$ gas that the desired temperature increase can be obtained over a heating hose length of approximately 2 m. This applies both with a zero flow as well as with a flow of 10 l/min to 18 or 20 l/min.

This phenomenon of an adequate heat transfer from the heating wire coil through the limited layer thickness the silicone to the $CO_2$ gas is due to the fact that $CO_2$, as a result of its high specific density of approximately 1.977 $kg/m^3$, has a largely laminar flow. The heat absorption of the $CO_2$ gas therefore mainly takes place by turbulence on the inner wall surface of the heating hose.

Thus, as a result of this surprising effect, with a zero flow and even after a prolonged stoppage there is only a relatively small, but desired heating. However, in the case of high flow rates the turbulence on the inner wall surface is very significant, so that the heat absorption of the $CO_2$ gas, which behaves like an unreal gas, occurs in the desired high level.

The heating hose is therefore connected with a length of 2 to 2.4 m directly to the outlet nipple of the insufflator. On the distal side the heating hose preferably has no heating coil over 1 to 2 cm. This ensures that the connected components, such as the torsional coupling, Veress needle, etc., are not subject to any undesired heating, and an electrical contact to the heating coil is eliminated in any case.

In said area a temperature sensor is advantageously integrated, but this must not bring about any additional turbulence, because this could falsify the measurements. In an optimum manner the temperature sensor line is integrated or extruded in the heating hose.

For stability and manufacturing standpoints the heating wire coils can be provided on a tubular textile or glass fibre-like mat, so that embedding between two hose casings can easily be achieved. Whereas the inner casing can be made from a somewhat less rigid silicone material, a more stable silicone material is chosen for the outer hose casing. However, it is ensured that there is no particle detachment or gas condensation on the inner wall area. In the case of a heating apparatus supplementary set the heating conductors are connected on the proximal side to a transformer with a voltage regulator or stabilizer and behind the rectification. It is sufficient on the secondary side to have a power of 20 Watt in the case of a d.c. voltage 20 V constant. As a result of the d.c. voltage used there is no electro-magnetic spurious radiation on other equipment.

However, in the ideal case the voltage supply of the heating wire coil would be brought about directly at the outlet nipple of the insufflator by contacted engagement of the hose onto the nipple. The voltage supply as well as the temperature reading on the distal side on the heating hose is integrated into the insufflator.

Advantageously the heating wire is designed as a PTC resistor or resistance wire, so that in the initial phase, particularly during the heating up period of approximately 10 min, there is an initially high current. With increasing heating the heating conductor resistance increases and the current drops to a roughly constant value. As a result in normal operation a lower heat output is required.

It is electrically advantageous to have a three-wire cable connection between the heating hose and the voltage supply; the third wire serves as an earth or discharge line when said hose is statically charged. As a result a higher mechanical compressive load is obtained at the collet of the plug.

A torsional coupling can be provided for a force decoupling between the Veress neeedle and the heating hose and said coupling compensates rotary movements and forces between the Veress needle and the heating hose.

BRIEF DESCRIPTION OF THE DRAWINGS

The invention is described in greater detail hereinafter relative to the drawings, wherein show:

FIG. 1 is a diagram of the pressure reduction in an insufflator with a heating hose provided at the outlet side.

FIG. 2 is a simplified representation of an insufflator with a connected heating hose, including the distal side Veress needle.

FIG. 3 is a radial section through an embodiment of a heating hose.

DESCRIPTION OF A PREFERRED EMBODIMENT

FIG. 1 shows a pressure cylinder 4 for liquid $CO_2$ gas. The gas temperature roughly corresponds to the ambient temperature of approximately 21° C., but there is a liquid vapour pressure of 40 to 60 bar depending on the room temperature. The $CO_2$ gas under 60 bar is expanded in a first pressure reducer 1 to approximately 0.8 bar, the temperature possibly dropping to about 0° C. The first pressure reducer is followed by a second pressure reducer 2 in the gas line 5, which brings about a further pressure reduction to approximately 50 mm/Hg. To the second pressure reducer 2 is connected a pressure regulator 3 making it possible to regulate the $CO_2$ gas to be insufflated in a pressure range of 0 mm/Hg to 14 or to 50 mm/Hg respectively.

At the outlet of said pressure regulator 3 the expanded $CO_2$ gas still has a temperature in the positive °C. range, but is below ambient temperature. To ensure that no relatively cold $CO_2$ gas is insufflated into the body, according to the invention a heating hose 10 with several heating wire coils 11 is connected to the outlet of the insufflator. For example, the Vetess needle 19 is connected to the heating hose 10 at the distal side.

So as to be able to use the heating hose 10 according to the invention on conventional insufflators, it is possible to provide a separate transformer 6, which on the primary side supplies the mains 7 with 220 V and on the secondary side, via a voltage regulator, 20 V d.c. voltage with an output of approximately 20 W.

In FIG. 2 the heating hose 10 is fitted directly to an insufflator 8 and namely to its gas connection 9. In the case of this heating hose, on the distal side a length region 17 of 1 to 2 cm does not have any heating wire coils 11. The gas connection 9 can also be a combined gas and measurement connection.

In order to equal out torsional forces in the case of a hose length of 2 m, on the distal side is provided a torsional coupling 18, which is connected to a Veress needle for insufflating gas into the body. There is a temperature sensor 21, e.g. a PT 100, which is connected by means of an integrated line provided in the heating hose 10 to the insufflator 8.

This also offers the possibility of regulating the heating power in the heating hose as a function of the flow and the temperature determined on the temperature sensor 21.

Thus, following an initial heating period of 15 to 20 min and an electrical wiring of approximately 20 V on the secondary side at approximately 1 A and a power of approximately 20 W, said heating hose 10 ensures a heating of the $CO_2$ gas virtually independently of the flow, to a temperature roughly corresponding to the body temperature. In radial section FIG. 3 shows an embodiment of the heating hose 10, which has an inner casing 13 and an outer casing 14, e.g. made from different silicone materials. Between the inner and outer casings are provided e.g. on a textile fibre mat six to eight heating wires 11 distributed over the circumference. Therefore these heating wires 11 are not directly, but indirectly in heat exchange by means of the relatively thin casing layer with the stationary $CO_2$ gas or the $CO_2$ gas flowing through the heating hose.

I claim:

1. A method for the insufflation of $CO_2$ gas into a biological body, wherein pressure of the gas is reduced by means of at least one pressure reducing stage and pressure-reduced gas is subsequently insufflated into the biological body, said method comprising:

heating the pressure-reduced gas to be insufflated to approximately the temperature of the biological body prior to insufflation into the biological body, wherein the heating step takes place directly before the gas enters into the biological body.

2. A method according to claim 1, comprising heating a hose line through which the passes over a distance of approximately 1.5 to 2.5 m.

3. A method according to claim 1, comprising heating the gas in a hose line constructed as a heating hose extending between an insufflator at one end thereof and an insufflator instrument for entering the body at the other end thereof.

4. An apparatus for heating pressure-reduced $CO_2$ gas to be introduced into a biological body, comprising an insufflator and a hose line extending therefrom, wherein the hose line is constructed as a heating hose (10) through which the gas passes during heating.

5. A heating apparatus according to claim 4, wherein the heating hose (10) has an inner wall surface and an integrated heating wire as a heating wire coil (11), which is provided in the vicinity of the inner wall surface (15).

6. A heating apparatus according to claim 5, wherein at least in an inner area thereof the heating hose (10) comprises a medically sterilizable silicone layer (13) in which the heating wire coil (11) is provided.

7. A heating apparatus according to claim 5, wherein the heating wire coil (11) is spaced from a distal area (17) of the heating hose (10) and in said distal area (17) a temperature sensor (21) having a sensor line integrated into the heating hose (10) is provided.

8. A heating apparatus according to claim 7, wherein the sensor line is coextruded in the heating hose.

9. A heating apparatus according to claim 5, wherein the heating wire (11) is designed as a PTC resistor with an approximately constant current consumption following a heating up time of approximately 10 min to 15 min.

10. A heating apparatus according to claim 5, wherein, at least in the inner area, the heating hose (10) has a medically sterilizable silicone layer (13) around which is placed the heating wire coil (11).

11. A heating apparatus according to claim 4, wherein the heating hose (10) has an inner and an outer plastic hose layer (13, 14) between which the heating wire coil (11) is provided.

12. A heating apparatus according to claim 11, wherein the inner and outer hose layers (13, 14) are extruded.

13. A heating apparatus according to claim 11, wherein the plastic is a silicone material.

14. A heating apparatus according to claim 11, wherein the plastic is a polyurethane material.

15. A heating apparatus according to claim 4, wherein the heating hose (10) has a length of approximately 1.8 to 2.5 m.

16. A heating apparatus according to claim 4, wherein the heating hose (10) is supplied with heating power of approximately 20 W for heating the $CO_2$ gas from approximately 20° C. up to 30° to 37° C.

17. A heating apparatus according to claim 4, wherein a torsional coupling (18) is provided at a distal side on the heating hose (10).

18. A heating apparatus according to claim 4, wherein a direct, electrical heating line connection is provided betweeen the heating hose (10) and the insufflator (8).

19. A heating apparatus according to claim 4, wherein the heating hose (10) comprises an electrically controllable heating hose.

20. A method for the insufflation of $N_2O$ gas into a biological body, in which the pressure of the gas is reduced to about 100 mm/Hg by means of at least one pressure reducing stage and subsequently insufflated into the biological body, wherein the gas to be insufflated is heated to the temperature of the biological body directly before being introduced into the biological body.

21. A method according to claim 20, comprising heating the gas in a hose line constructed as a heating hose extending between an insufflator at one end thereof and an insufflator instrument for entering the body at the other end thereof.

22. A method for the insufflation of a gas selected from $CO_2$ and $N_2O$ into a biological body by means of an insufflator, a hose line for the gas having a first end extending from an insufflator and a second end secured to an insufflator instrument for entering the gas into the biological body, comprising:

reducing the pressure of the gas to be insufflated in at least one pressure reducing stage, passing the pressure-reduced gas through the hose line;

heating the pressure-reduced gas in said hose line to approximately the temperature of the biological body prior to insufflation into the biological body, said hose line being constructed as a heating hose.

23. An apparatus for heating pressure-reduced gas selected from $CO_2$ and $N_2O$ to be introduced by insufflation into a biological body, said apparatus comprising a heating hose for transporting and heating the pressure-reduced gas, said hose having a first end adapted for securing to an insufflator and a second end adapted for securing to an insufflator instrument which is inserted into the biological body, wherein as the pressure-reduced gas flows through the heating hose from the insufflator to the insufflator instrument, the gas is heated to a predetermined temperature measured in the region of the insufflator instrument.

* * * * *